(12) United States Patent
Winnicki

(10) Patent No.: US 9,095,555 B2
(45) Date of Patent: Aug. 4, 2015

(54) CANNABINOID FORMULATIONS

(71) Applicant: FULL SPECTRUM LABORATORIES LIMITED, Dublin (IE)

(72) Inventor: Robert Winnicki, Denver, CO (US)

(73) Assignee: FULL SPECTRUM LABORATORIES, LIMITED, Dublin (IE)

( * ) Notice: Subject to any disclaimer, the term of this patent is extended or adjusted under 35 U.S.C. 154(b) by 0 days.

(21) Appl. No.: 14/312,570

(22) Filed: Jun. 23, 2014

(65) Prior Publication Data

US 2014/0302148 A1  Oct. 9, 2014

Related U.S. Application Data

(62) Division of application No. 13/547,039, filed on Jul. 11, 2012, now Pat. No. 8,808,734.

(60) Provisional application No. 61/506,331, filed on Jul. 11, 2011.

(51) Int. Cl.

| | |
|---|---|
| A61K 36/185 | (2006.01) |
| A61K 9/127 | (2006.01) |
| A61K 31/352 | (2006.01) |
| A61K 31/05 | (2006.01) |
| A23L 1/30 | (2006.01) |
| A61K 47/10 | (2006.01) |
| A61K 47/24 | (2006.01) |
| A61K 47/36 | (2006.01) |
| A61K 9/107 | (2006.01) |
| A61K 45/06 | (2006.01) |

(52) U.S. Cl.
CPC ............. *A61K 36/185* (2013.01); *A23L 1/3002* (2013.01); *A61K 9/107* (2013.01); *A61K 9/1075* (2013.01); *A61K 9/127* (2013.01); *A61K 31/05* (2013.01); *A61K 31/352* (2013.01); *A61K 45/06* (2013.01); *A61K 47/10* (2013.01); *A61K 47/24* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 5,464,629 A | 11/1995 | Monshipouri et al. | |
| 5,506,217 A | 4/1996 | Salari et al. | |
| 5,800,833 A | 9/1998 | Hope et al. | |
| 2003/0068365 A1 | 4/2003 | Suvanprakorn et al. | |
| 2006/0240092 A1* | 10/2006 | Breitenkamp et al. | 424/450 |
| 2008/0112895 A1* | 5/2008 | Kottayil et al. | 424/46 |
| 2008/0241339 A1 | 10/2008 | Mitchell et al. | |
| 2009/0169629 A1* | 7/2009 | Lambert et al. | 424/489 |
| 2011/0070294 A1 | 3/2011 | Javeri et al. | |

FOREIGN PATENT DOCUMENTS

| | | |
|---|---|---|
| WO | WO 01/03668 A1 | 1/2001 |
| WO | WO 2006/063596 A2 | 6/2006 |
| WO | WO 2009/027337 A1 | 3/2009 |

OTHER PUBLICATIONS

M Pasquali. "Go With the Flow." Nature Materials, vol. 9, May 2010, pp. 381-382.*
Batzi, et al., "Interaction of Phospholipid vesicles with cells", *J Cell Biol.*, 1975, vol. 66, pp. 621-634.

* cited by examiner

*Primary Examiner* — Isaac Shomer
(74) *Attorney, Agent, or Firm* — Foley & Lardner LLP

(57) ABSTRACT

The present invention provides stable, fast-acting liposomal and micelle formulations of cannabinoids that are suitable for pharmaceutical and nutraceutical applications.

8 Claims, 3 Drawing Sheets

CANNABINOID FORMULATIONS

This application is a Divisional Application of U.S. patent application Ser. No. 13/547,039, filed Jul. 11, 2012, which claims priority to U.S. Provisional Application No. 61/506,331, filed on Jul. 11, 2011. The contents of all priority applications are incorporated herein by reference in their entirety.

FIELD OF THE INVENTION

The present invention relates to liposomal and micelle formulations of cannabinoids suitable for pharmaceutical and nutraceutical applications.

BACKGROUND OF THE INVENTION

Cannabinoids are compounds derived from *Cannabis sativa*, an annual plant in the Cannabaceae family. The plant contains about 60 cannabinoids. The most active naturally occurring cannabinoid is tetrahydrocannabinol (THC), which is used for the treatment of a wide range of medical conditions, including glaucoma, AIDS wasting, neuropathic pain, treatment of spasticity associated with multiple sclerosis, fibromyalgia and chemotherapy-induced nausea. Additionally, THC has been reported to exhibit a therapeutic effect in the treatment of allergies, inflammation, infection, epilepsy, depression, migraine, bipolar disorders, anxiety disorder, and drug dependency and withdrawal syndromes. THC is particularly effective as an anti-emetic drug and is administered to curb emesis, a common side effect accompanying the use of opioid analgesics and anaesthetics, highly active anti-retroviral therapy and cancer chemotherapy.

Cannabinoids are lipophilic and potentially acid-labile compounds. Because of their hydrophobic nature, cannabinoids are poorly absorbed systemically from oral dosage forms because of the poor dissolution of cannabinoids in the aqueous environment of gastrointestinal tract. Oral formulations of cannabinoids, therefore, exhibit low bioavailability.

$\Delta^9$-tetrahydrocannabinol is prone to oxidation, Prolonged contact with air results in the gradual oxidation of $\Delta^9$-tetrahydrocannabinol to cannabinol (CBN). There are currently two oral formulations of $\Delta^9$-tetrahydrocannabinol commercially available by prescription in the United States: Dronabinol, is available commercially as Marinol®™ soft gelatin capsules and Namisol®™ is available as sublingual tablets, have been approved by the Food and Drug Administration (FDA) for the control of nausea and vomiting associated with chemotherapy and for appetite stimulation in AIDS patients suffering from the wasting syndrome. Marinol®™ is formulated by dissolving $\Delta^9$-tetrahydrocannabinol in sesame oil to manufacture soft gelatin capsules suitable for oral administration. Marinol®™ is expensive and gelatin capsules of Marinol®™ exhibit full therapeutic potency approximately one hour following their administration.

Onset of therapeutic potency for Dronabinol is shorter, approximately 0.5 to 1 hour after oral administration, with a peak therapeutic effect lasting for a time period of 2-4 hours post administration. However, the amount of Dronabinol reaching the blood stream by absorption through the digestive system is only 10-20% of the administered dose. Fasting or food deprivation may further decrease the rate of absorption of Dronabinol.

On the other hand, Namisol®™ has a rapid uptake through the sublingual mucosa. However, the tablet, has to be kept under the tongue for the time it takes to dissolve and stimulates the flow of saliva. This make it difficult for patients to avoid swallowing the tablet when substantial amounts of saliva are produced.

Oral formulations of synthetic cannabionoids are also available commercially. For instance, Nabilone is a synthetic cannabinoid marketed as Cesamet® in Canada the United States, the United Kingdom and Mexico. Nabilone is formulated as capsules suitable for oral administration. Cesamet® is approved for use as an antiemetic and analgesic for neuropathic pain. Sativex®, is a mouth spray containing tetrahydrocannabinol (THC) and cannabidiol (CBD). It is approved for the treatment of spasticity due to multiple sclerosis. Administration of synthetic cannabinoid formulations show fewer undesirable side effects than THC.

Because of their poor absorbtion and poor bioavailability, oral formulations have the additional disadvantage that they require several administrations a day, making it inconvenient for patients who have difficulty swallowing.

Accordingly, there is an urgent need in the art for oral formulations of cannabinoids with improved dissolution and taste and enhanced bioavailability and absorption, while at the same time do not cause gastrointestinal irritation. The present invention satisfies this need.

SUMMARY OF THE INVENTION

It is therefore an object of the invention to provide solutions to the aforementioned deficiencies in the art. To this end the invention provides a stable, aqueous micelle suspension of one or more cannabinoids or cannabinoid analogues, wherein the stable aqueous micelle suspension of one or more cannabinoids or cannabinoid analogues does not comprise phospholipids and cholesterol. For the inventive compositions, the average micelle diameter size is in a range between 50 and 1000 nm.

According to one embodiment, the final maximum concentration of cannabinoids or cannabinoid analogues in the aqueous micelle suspension of one or more cannabinoids or cannabinoid analogues is 2 g/liter. The cannabinoids or cannabinoid analogues are a natural compound, a synthetic compound, a semi-synthetic compound, or mixtures thereof. Illustrative of cannabinoids or cannabinoid analogues are compounds selected from the group consisting of cannabinol, cannabidiol, Δ9-tetrahydrocannabinol, Δ9-tetrahydrocannabinol, 11-hydroxy-tetrahydrocannabinol, 11-bydroxy-Δ9-tetrahydrocannabinol, levonantradol, Δ11-tetrahydrocannabinol, tetranydrocannabinol, tetrahydrocannabivarin, dronabinol, amandamide, nabilone, a combination thereof, a natural or synthetic analogue thereof, and a natural or synthetic molecule with a basic cannabinoid structure.

In one embodiment the stable aqueous micelle suspension of one or more cannabinoids or cannabinoid analogues further comprises a stabilizer selected from the group consisting of guar gum, xyanthan gum cellulose hyaluronic acid, polyvinyl pyrrolidone (PVP), alginate, chondritin sulfate, poly gamma glutamic acid, gelatin, chitisin, corn starch and flour, in an amount from about 0.25% to about 2% (w/v).

In yet another embodiment is provided a method of producing a stable aqueous micelle suspension of one or more cannabinoids or cannabinoid analogues that is devoid of phospholipids and cholesterol. The inventive method comprises the steps of (a) dissolving one or more cannabinoids or cannabinoid analogues in ethanol to obtain an ethanol cannabinoid solution; (b) injecting the ethanol cannabinoid solution into distilled water to obtain a micelle cannabinoid aqueous suspension; and (c) removing the ethanol from the cannabinoid aqueous suspension thereby producing a stable aqueous micelle suspension of one or more cannabinoids or cannabinoid analogues. The aqueous micelle suspension do not contain phospholipids and cholesterol and are devoid of an aqueous core under oil immersion microscopy.

According to one embodiment, the average micelle diameter size in the aqueous micelle suspension of one or more cannabinoids or cannabinoid analogues is in a range between 50 and 1000 nm, and the final maximum concentration of cannabinoids or cannabinoid analogues in the aqueous micelle suspension of one or more cannabinoids or cannabinoid analogues is 2 g/liter. The one or more cannabinoids or cannabinoid analogues of the present invention are a natural compound, a synthetic compound, a semi-synthetic compound, or mixtures thereof. Illustrative of such compounds are cannabinoids or cannabinoid analogues selected from the group consisting of cannabinol, cannabidiol, Δ9-tetrahydrocannabinol, Δ8-tetrahydrocannabinol, hydroxy-tetrahydrocannabinol, 11-hydroxy-Δ9-tetrahydrocannabinol, levonantradol, Δ11-tetrahydrocannabinol, tetrahydrocannabivarin, dronabinol, amandamide, nabilone, a combination thereof, a natural or synthetic analogue thereof, and a natural or synthetic molecule with a basic cannabinoid structure.

The present invention in one of its embodiments provides a highly concentrated liposomal formulation of one or more cannabinoids or cannabinoid analogues, with final maximum concentrationd of cannabinoids or cannabinoid analogues in the liposomal suspension being 50 g/liter. The one or more cannabinoids or cannabinoid analogues in the inventive composition are a natural compound, a synthetic compound, a semi-synthetic compound, or mixtures thereof. Illustrative of such compounds are cannabinoids or cannabinoid analogues selected from the group consisting of cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, dronabinol, amandamide, nabilone, a combination thereof, a natural or synthetic analogue thereof, and a natural or synthetic molecule with a basic cannabinoid structure.

The average diameter size of liposomes in the inventive composition is from about 200 to about 400 nm. For these compositions the maximum phospholipid content of the hydrophobic/lipophilic membrane is 50% of the total composition and the hydrophobic/lipophilic membrane comprises about 26% phosphatidylcholine, about 10% phosphatidylethanolamine, about 13% phosphonophospholipids, and about 1% of other phospholipids.

Also provided as an embodiment of the present technology is a method of producing a stable, highly concentrated liposomal formulation of one or more cannabinoids or cannabinoid analogues by (a) dissolving one or more cannabinoids or cannabinoid analogues in ethanol to obtain an ethanol cannabinoid solution; (b) adding a phospholipid to the ethanol cannabinoid solution to obtain an ethanol-phospholipid cannabinoid solution; (c) injecting the ethanol-phospholipid cannabinoid solution into distilled water to obtain a liposomal cannabinoid suspension; and (d) removing the ethanol from the liposomal cannabinoid suspension, thereby producing a stable liposomal suspension of one or more cannabinoids or cannabinoid analogues;

The final maximum concentration of cannabinoids or cannabinoid analogues in the liposomal suspension is 50 g/liter and the one or more cannabinoids or cannabinoid analogues are a natural compound, a synthetic compound, a semi-synthetic compound, or mixtures thereof. Preferably the cannabinoids or cannabinoid analogues are selected from the group consisting of cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabinol, tetrahydrocannabivarin, dronabinol, amandamide, nabilone, a combination thereof, a natural or synthetic analogue thereof, and a natural or synthetic molecule with a basic cannabinoid structure.

The inventive method further comprises the step of adding sodium alginate to the liposomal suspension of one or more cannabinoids or cannabinoid analogues to obtain an alginate liposomal cannabinoid suspension that has a final alginate concentration of 2% w/v, followed by the addition of calcium chloride to the alginate liposomal cannabinoid suspension to obtain a calcium alginate-encapsulated liposomal cannabinoid suspension. This suspension is then cold-pressed and air-dried to remove the water so as to obtain a dry cannabinoid powder. The dry cannabinoid powder can be re-suspended in citrate buffer to obtain an aqueous cannabinoid solution. The amount of cannabinoid or cannabinoid analogue in the aqueous cannabinoid solution is greater than 40%.

According to an embodiment of the inventive method, sodium alginate is added to the liposomal suspension of one or more cannabinoids or cannabinoid analogues to obtain an alginate liposomal cannabinoid suspension that has a final alginate concentration of 4% w/v. Shell-freezing of this solution using dry ice or in acetone bath and freeze-drying to remove water provides a dry cannabinoid powder that is milled and can be re-suspended in water to obtain an aqueous cannabinoid solution. The amount of cannabinoid or cannabinoid analogue in the aqueous cannabinoid solution is greater than 40%.

In one embodiment, L-leucine and a sugar are added to the liposomal suspension of one or more cannabinoids or cannabinoid analogues to obtain a sugar liposomal cannabinoid suspension The sugar is selected from the group consisting of lactose and sucrose. Shell-freezing the sugar liposomal cannabinoid suspension over dry ice acetone bath and freeze-drying the suspension to remove the water provides a dry cannabinoid powder that is milled and can be re-suspended in water to obtain an aqueous cannabinoid solution. The amount of cannabinoids or cannabinoid analogues in the aqueous solution is 50 g/liter.

Such an aqueous cannabinoid solution can be in the form of a fast-acting pharmaceutical composition, a nutraceutical composition, or a food or beverage for administration to a subject. Illustrative of food containing the aqueous cannabinoid solution are foods selected from a soup, a baking good, a dairy product, a meat product, a fish product, a vegetable product or a fruit product. The aqueous cannabinoid solution formulated as pharmaceutical composition, a nutraceutical composition, or a food or beverage are fast-acting formulations for oral, enteral, parenteral, intravenous, pulmonary, mucosal, sub-mucosal or topical administration.

In yet another embodiment, the invention provides a method of alleviating pain or reducing undesirable side effects associated with radiation therapy or chemotherapy in a subject in need thereof comprising administering to the subject the aqueous cannabinoid solution as described above. Subjects treated using the inventive method have a compromised immune system, a cancer, a pulmonary disease or a condition that causes violent tremors.

The foregoing general description and following brief description of the drawings and the detailed description are exemplary and explanatory and are intended to provide further explanation of the invention as claimed. Other objects, advantages, and novel features will be readily apparent to those skilled in the art from the following detailed description of the invention.

DETAILED DESCRIPTION OF THE PREFERRED EMBODIMENTS

Figure 1:
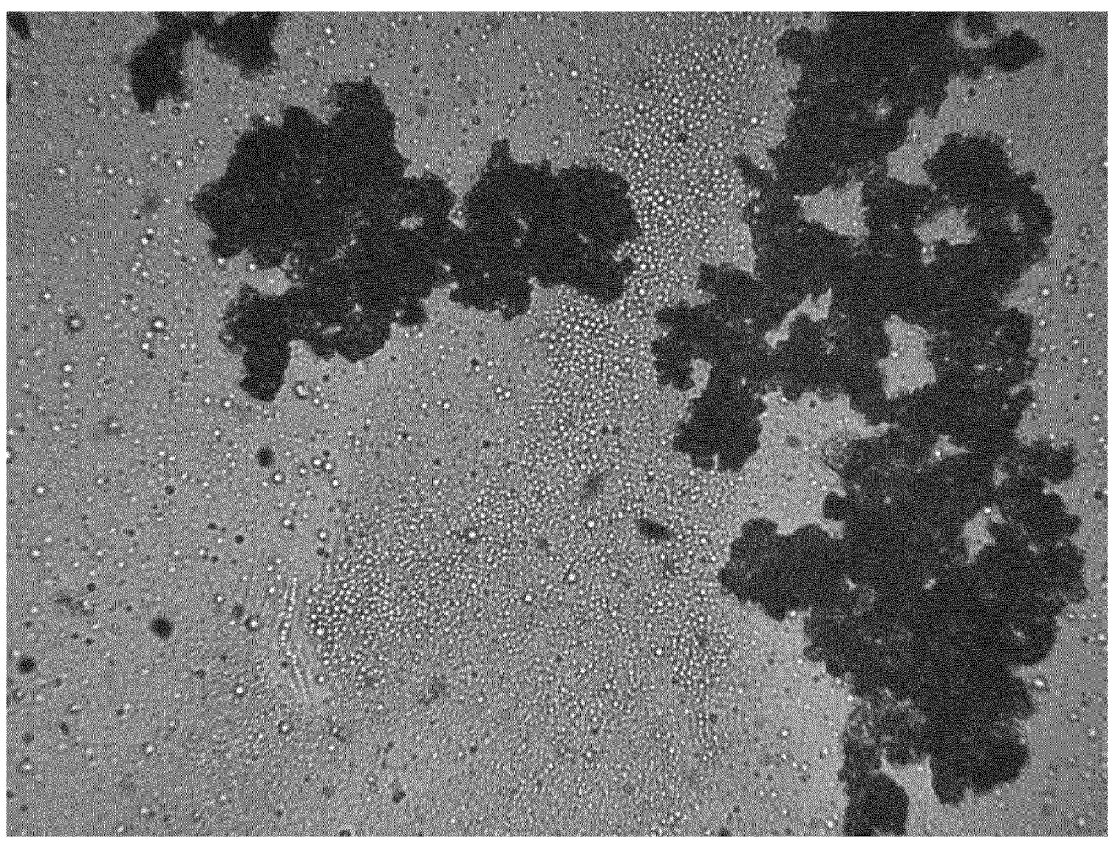
FIG. 1 provides an oil immersion image of a micelle suspension stained with fast blue as seen through a red filter.

The present invention provides stable, fast-acting formulation of a cannabinoid or a cannabinoid analog. The term "analog" refers to compound that is structurally related to naturally occurring cannabinoids, but whose chemical and biological properties may differ from naturally occurring cannabinoids. In the present context, analog or analogs refer compounds that may not exhibit one or more unwanted side effects of a naturally occurring cannabinoid. Analog also refers to a compound that is derived from a naturally occurring cannabinoid by chemical, biological or a semi-synthetic transformation of the naturally occurring cannabinoid. According to one aspect, therefore, are provided liquid compositions of cannabinoids and their analogs. The present invention also provides stable colloidal formulations that are manufactured by contacting a solution containing a cannabinoid, its analog, or both into a solvent such as water, with or without pharmaceutically acceptable buffers. Any solvent such as $C1$-$C_6$ aliphatic alcohols or mixtures of water and alcohols, acetone or any water miscible organic solvent can be used to dissolve the cannabinoids.

The inventive cannabinoid formulations are in the form of micelles or liposomes that encapsulate a cannabinoid or its analog within the membrane of the micelles or liposomes. Within the context of the present technology, the term "micelle" refers to an aggregate of surfactant molecules dispersed in a liquid colloid, while "liposome" refers to a vesicle composed of a mono or bilayer lipid.

Other drugs, and pharmaceutically acceptable carriers if present, may be in the lipophilic membrane or entrapped in the aqueous fluid that forms the core of the liposome. The entrapped cannabinoids contribute to the stability of the micelle/liposome membranes, such that the micelle/liposomes formulations may be used as an improved, fast, reliable and efficient system for the oral, enteral, parenteral, intravenous or topical delivery of cannabinoids and/or additional drugs to subjects in need thereof. The term "subject" refers to a mammal in need of treatment or undergoing treatment using the inventive compositions. Mammalian subjects include without limitation humans, dog, cat, horse or any other animal in need of treatment.

Unilamellar micelles or liposomes that are thermostable at temperatures greater than 50° C. are used in the manufacture of cannabinoid formulations according to the present invention. These micelles or liposomes are obtained by contacting a solution of a cannabinoid, its analog or both (a cannabinoid extract), with an aqueous solvent or an aqueous solution of a pharmaceutically active compound or drug. The mixing of the cannabinoid solution occurs in a manner suitable for the rapid dissolution of the cannabinoid solution in the aqueous solution. This can be accomplished through a variety of means including dilution, injection through a small orifice under pressure, and ultrasonic atomization.

For certain embodiments, the inventive composition is in the form of a concentrated, stable colloidal suspension that is obtained by infusing a solvent solution containing the cannabinoid extract or pure cannabinoids into a solvent such as water, with or without buffer. Stabilizing agent, for instance, a polymer or compounds selected from cellulose hyaluronic acid, polyvinyl pyrrolidone (PVP), alginate, chondritin sulfate, poly gamma glutamic acid, gelatin, chitisin, corn starch and flour can be used to stabilize the micelle formulations.

Typically, the size of the inventive micelles is from about 0.01 μm to about 2.0 μm. For certain embodiments, the size of the spherical micelles is about 0.05 μm, about 0.1 μm, about 0.15 μm, 0.2 μm, 0.25 μm, 0.3 μm, 0.35 μm, 0.4 μm, 0.45 μm, 0.5 μm, 0.55 μm, 0.6 μm, 0.7 μm, 0.75 μm, 0.8 μm, 0.85 μm, 0.9 μm, about 0.95 μm, about 1.0 μm, 1.20 μm, 1.40 μm, 1.50 μm, 1.60 μm, 1.70 μm, 1.80 μm, 1.90 μm and 2.0 μm. For certain embodiments, micelles that are about 0.04 μm, about 0.05 μm, about 0.06 μm, about 0.07 μm, about 0.08 μm, or about 0.09 μm are used to formulate the inventive compositions.

According to one aspect, the maximum final concentration of a cannabinoids or an analog of the cannabinoid in the micellar colloidal suspension is from about 1.0 mg/mL to about 10.0 mg/mL both values inclusive. For some embodiments, the concentration of a cannabinoid extract within the inventive micelles is about 1.0 mg/mL, about 2.0 mg/mL, about 3.0 mg/mL, 4.0 mg/mL, about 5.0 mg/mL, about 6.0 mg/mL, about 7.0 mg/mL, about 8.0 mg/mL, or about 9.0 mg/mL.

Typical concentrations of cannabinoids within a liposomal suspension according to the present invention are about 50 mg/mL. For certain embodiments, the maximum final concentration of cannabinoids or an analog of the cannabinoid in the liposomal formulation is from about 10.0 mg/mL to about 300.0 mg/mL both values inclusive, for example, about 15.0 mg/mL, about 20.0 mg/mL, about 30.0 mg/mL, about 40.0 mg/mL, about 50.0 mg/mL, about 60.0 mg/mL, about 70.0 mg/mL, about 80.0 mg/mL, about 90.0 mg/mL, about 150.0 mg/mL, about 200.0 mg/mL, about 250.0 mg/mL, or about 300.0 mg/mL.

For liposomal compositions according to this invention, the size of the unilamellar spherical liposome is from about 0.1 μm to about 2.0 μm both values inclusive, such as about 0.15 μm, about 0.2 μm, about 0.22 μm, about 0.25 μm, about 0.3 μm, about 0.32 μm, about 0.35 μm, about 0.4 μm, about 0.42 μm, about 0.45 μm, about 0.5 μm, about 0.52 μm, about 0.55 μm, about 0.6 μm, about 0.7 μm, about 0.75 μm, about 0.8 μm, about 0.85 μm, about 0.9 μm, about 0.95 μm, about 1.0 μm, about 1.1 μm, about 1.2 μm, about 1.3 μm, about 1.4 μm, about 1.5 μm, about 1.6 μm, about 1.7 μm, about 1.8 μm, about 1.9 μm, or about 2.0 μm.

The formulations of the invention are therefore particularly suitable for oral administration and may be administered to subjects with a pre-existing condition or pre-disposed to certain disease conditions, acute pain, or chronic pain conditions. Conditions contemplated by the invention include, but are not limited to, gastrointestinal, metabolic, neurological, circulatory, soft tissue, musculoskeletal, chronic or acute pain, nausea, decreased appetite, skin disorders, sexual dysfunction, glaucoma, AIDS wasting, neuropathic pain, treatment of spasticity associated with multiple sclerosis, fibromyalgia, chemotherapy-induced nausea, allergies, inflammation, infection, epilepsy, depression, migraine, bipolar disorders, anxiety disorder, dependency and withdrawal. In addition, the methods of the invention may be used to alleviate or relief symptoms or side effects associated with anti-retroviral therapy, chemotherapy and radiation therapy.

Illustrative of cannabinoid compounds include without limitation cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonantradol, Δ11-tetrahydrocannabinol, tetrahydrocannabivarin, dronabinol, amandamide, nabilone, any combination thereof, any natural or synthetic modification thereof, or any natural or synthetic molecule with a basic cannabinoid structure. In a preferred embodiment, the cannabinoid is tetrahydrocannabinol (THC).

Natural cannabinoid compounds used in the inventive compositions are readily obtained from plant tissue, for example, trichones of the *C. sativa* plant, by suspending the tissue in an appropriate solvent to extract cannabinoid compounds and other tissue components. Analytical purification of such an extract provides pharmaceutical grade cannabinoid compounds. Alternatively, cannabinoid compounds are extracted from plant tissue under supercritical conditions. Solvents used for supercritical extraction of cannabinoids include without limitation carbon dioxide, or other gases in isolation or combination with or without solvent modifiers, selected from ethanol, propanol, butanol, hexane, chloroform, dichloromethane, acetone, or any organic solvent capable of extracting cannabinoids, and alcohol-water mixtures, for instance water-ethanol or water-butanol mixtures.

In addition to natural cannabinoids, the present technology encompasses synthetic cannabinoid compounds as well as cannabinoids and their analogs that are obtained using semi-synthetic protocols. The manufacture of cannabinoid compounds and their analogs using semi-synthetic means involves contacting an appropriate substrate with one of the cannabinoid synthase enzymes. For instance, tetrahydrocannabinolic acid (THCA) or its analogs can be manufactured semi-synthetically by contacting cannabigerolic acid (CBGA) or an appropriately substituted derivative of CBGA with THC synthase to obtain the corresponding THCA or THCA analog respectively. The inventive compositions may also contain natural or synthetically modified cannabinoids.

The inventive compositions have unexpected advantageous properties. For instance, micellar and liposomal compositions according to the present invention are stable at high temperatures, exceeding 50° C., are stable to sonication, capable of carrying large payloads of cannabinoids as well as other drug suitable for use in combination therapy and can be stored for extended periods of time, for example greater than 20 weeks at 25° C.

The inventive compositions also exhibit superior systemic delivery and release of cannabinoids from the micelle or liposomes used in the manufacture of the inventive composition. The release of a cannabinoid from a liposome or micelle of the inventive composition can be modulated by changing the ratio of the concentration of lipid to the concentration of cannabinoid present in the liposome.

In one embodiment, tissue specific delivery can be achieved by modifying the surface of the liposomes or micelles with compounds that bind specifically to biological macromolecules expressed on cellular surfaces. For instance, the micelle or liposomal surface can be derivatized to display an antibody specific to an antigen expressed on cancer cells.

According to one embodiment, compositions of the present invention are used in the treatment of disease conditions. For instance, an inventive composition of the cannabinoid extract, (cannabinoid, an analog of a cannabinoid, or both), can be administered to a patient or subject in need of treatment either alone or in combination with other compounds/drugs having similar or different biological activities.

For example, compositions of the invention may be administered in a combination therapy, i.e., either simultaneously in single or separate dosage forms or in separate dosage forms within hours or days of each other. Examples of compounds/drugs used in such combination therapies include without limitation, chemotherapeutic agents, immunosuppressive agents, immunostimulatory, anti pyretic, cytokines, opioids, cytokines, cytotoxic agents, nucleolytic compounds, radioactive isotopes, receptors, pro-drug activating enzymes, which may be naturally occurring or produced by recombinant methods, anti-inflammatory agents, antibiotics, protease inhibitors, growth factors, osteo-inductive factors and the like.

In some embodiments, the composition further contains, in accordance with accepted practices of pharmaceutical compounding, one or more pharmaceutically acceptable excipients, diluents, adjuvants, stabilizers, emulsifiers, preservatives, colorants, buffers, flavor imparting agents. As stated above, the inventive compositions may contain a cannabinoid, an analog of a cannabinoid, or both and may be consumed directly or formulated into nutraceutical or pharmaceutically acceptable compositions suitable for oral, enteral, parenteral, intravenous or topical administration.

The term parenteral as used herein includes subcutaneous injections, intravenous, intramuscular, intrasternal injection or infusion techniques. Such excipients are well known in the art. Dosage forms for oral administration include food, beverages, drinks, soups, baked goods, syrups, oral pharmaceutical compositions, nutraceutical formulations, and the like. Suitable pharmaceutical carriers include any such materials known in the art, e.g., any liquid, gel, solvent, liquid diluent, solubilizer, polymer or the like, which is non-toxic and which does not significantly interact with other components of the formulations in a deleterious manner.

Liquid dosage forms for oral administration include, but are not limited to, pharmaceutically acceptable emulsions, solutions, suspensions, syrups and elixirs. In addition to the cannabinoid extract, the liquid dosage forms can contain inert diluents commonly used in the art. For instance, liquid formulations can contain water, alcohol, polyethylene glycol ethers, or any other pharmaceutically acceptable solvents. Solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof may also be present in the inventive compositions. Additionally, oral compositions can include adjuvants such as wetting agents, emulsifying and suspending agents, sweetening, flavoring, and perfuming agents. When formulated as a suspension, the inventive compositions contain the cannabinoid extract and suspending agents, for example, ethoxylated isostearyl alcohols, polyoxyethylene sorbitol, sorbitan esters, microcrystalline cellulose, aluminum metahydroxide, bentonite, agar-agar, tragacanth, and mixtures thereof.

Solid dosage forms suitable for oral administration include, capsules, tablets, pills, powders, and granules. In such solid dosage forms, the cannabinoid extract, for instance, a cannabinoid or a cannabinoid analog can be used alone or in combination with one or more drugs are mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For capsules, tablets and pills, the dosage form can also comprise buffering agents.

Micellular or liposomal suspensions can be encapsulated with a variety of polymers, sugars, and chelating agents, to yield stable solid liposomal cannabinoid preparation. Encapsulation can take the form of cross linked polymers, trapping of the micells or liposomes within a non crosslinked polymer network, or dispersed within the crystalline structer of sugar starches or protein molecules. These granulas can be further process to yield sublingual films, suppositories, dispersable powder, tablets, gel capsules, etc.

Solid dosages in the form of tablets, dragees, capsules, pills, and granules can be coated using compounds that accelerate or decrease the release of cannabinoids. For instance, the invention encompases solid dosage forms having enteric coatings, extended-release coatings, sustained-release coatings, delayed release coatings and immediate-release coatings. Methods used to coat solid dosage forms as well as the materials used to manufacture such coatings are well known in the pharmaceutical formulary art. The solid dosage forms can optionally contain opacity enhancing agents. According to an embodiment, the solid dosage form comprises an enteric coating that permits the release of a cannabinoid or cannabinoid analog alone or in combination with one or more drugs at a specific location within the gastrointestinal tract, optionally, in a delayed manner. Exemplary of such coating materials include glyceryl monostearate or glyceryl distearate may be employed, polymeric substances and waxes. The cannabinoid extract, for instance, a cannabinoid or cannabinoid analog alone or in combination with one or more drugs can also be in micro-encapsulated form, if appropriate, with one or more of the above-mentioned excipients.

A dietary composition according to the present invention is any ingestible preparation that contains the cannabinoid suspensions of the invention mixed with a food product. The food product can be dried, cooked, boiled, lyophilized or baked. Breads, teas, soups, cereals, salads, sandwiches, sprouts, vegetables, animal feed, pills and tablets, are among the vast number of different food products contemplated in the present invention.

Compositions for parenteral injection comprise pharmaceutically acceptable sterile aqueous or nonaqueous solutions, dispersions, suspensions or emulsions as well as sterile powders for reconstitution into sterile injectable solutions or dispersions prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants. The compositions of the present invention can also contain adjuvants such as, but not limited to, preservatives, wetting agents, emulsifying agents, and dispersing agents. Compositions for parenteral delivery generally include isotonic agents such as sugars, sodium chloride, and the like. Prolonged absorption of the injectable pharmaceutical formulation can be brought about by the inclusion of agents which delay absorption such as aluminum monostearate and gelatin.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Dosage forms for topical administration include, but are not limited to, ointments, creams, emulsions, lotions, gels, sunscreens and agents that favor penetration within the epidermis. Various additives, known to those skilled in the art, may be included in the topical formulations of the invention. Examples of additives include, but are not limited to, solubilizers, skin permeation enhancers, preservatives (e.g., antioxidants), moisturizers, gelling agents, buffering agents, surfactants, emulsifiers, emollients, thickening agents, stabilizers, humectants, dispersing agents and pharmaceutical carriers. Examples of moisturizers include jojoba oil and evening primrose oil. Suitable skin permeation enhancers are well known in the art and include lower alkanols, such as methanol ethanol and 2-propanol; alkyl methyl sulfoxides such as dimethylsulfoxide (DMSO), decylmethylsulfoxide (C10 MSO) and tetradecylmethyl sulfoxide; pyrrolidones, urea; N,N-diethyl-m-toluamide; C2-C6 alkanediols; dimethyl formamide (DMF), N,N-dimethylacetamide (DMA) and tetrahydrofurfuryl alcohol. Examples of solubilizers include, but are not limited to, hydrophilic ethers such as diethylene glycol monoethyl ether (ethoxydiglycol, available commercially as Transcutol®) and diethylene glycol monoethyl ether oleate (available commercially as Softcutol®); polyoxy 35 castor oil, polyoxy 40 hydrogenated castor oil, polyethylene glycol (PEG), particularly low molecular weight PEGs, such as PEG 300 and PEG 400, and polyethylene glycol derivatives such as PEG-8 caprylic/capric glycerides (available commercially as Labrasol®); alkyl methyl sulfoxides, such as DMSO; pyrrolidones, DMA, and mixtures thereof.

Prevention and/or treatment of infections can be achieved by the inclusion of antibiotics, as well as various antibacterial and antifungal agents, for example, paraben, chlorobutanol, phenol sorbic acid, and the like, in the compositions of the invention.

One of ordinary skill will appreciate that effective amounts of the agents in the compositions used in the methods of the invention can be determined empirically. It will be understood that, when administered to a human patient, the total daily usage of the composition of the present invention will be decided by the attending physician within the scope of sound medical judgment. The specific therapeutically effective dose level for any particular patient will depend upon a variety of factors: the type and degree of the response to be achieved; the activity of the specific composition employed; the age, body weight, general health, sex and diet of the patient; the duration of the treatment; drugs used in combination or coincidental with the method of the invention; and like factors well known in the medical arts.

The potential commercial uses of the disclosed preparations include, for example, protective/prophylactic and medical uses. The compositions of the invention can also be administered by a variety of other routes, including mucosal, subcutaneous and intramuscular administration, and may comprise a variety of carriers or excipients known in the formulary art, such as, non-toxic solid, semisolid or liquid filler, diluent, encapsulating material and formulation auxiliaries that are pharmaceutically acceptable.

The present invention thus generally described, will be understood more readily by reference to the following examples, which are provided by way of illustration only, and are not intended to be limiting the present invention.

EXAMPLES

A. General Protocol for the Manufacture of Micelles

A cannabinoid, its analog or cannabinoid extract are dissolved in a water miscible organic solvent. This solvent cannabinoid solution is rapidly mixed or injected into an appropriate aqueous environment. The rapid dissolution of the organic solvent causes the dissolved cannabinoids to self align into micro or nano micellar particles. Size, composition and concentration of the micells are controlled by the chemical properties of the cannabinoids, the organic solvent/aqueous environment and the physical parameters of the solvent addition.

B. General Protocol for the Manufacture of Liposomes

Pure Cannabinoids or cannabinoid extracts are dissolved in a water miscible organic solvent. To this solution various amphipathic molecules such as phospholipids, sterols, and/or fatty acids are also dissolved. This solution containing the cannabinoids and amphipathic molecules is rapidly mixed or injected into an appropriate aqueous environment. The rapid dissolution of the organic solvent causes the dissolved cannabinoids and amphipathic molecules initiates the spontaneous formation of ordered lipid layers which self assemble into micro or nano liposomal particles. The size, composition and concentration of the liposomes are controlled by the chemical properties and relative concentrations of the cannabinoids and lipids, the organic solvent/aqueous environment and the physical parameters of the solvent addition.

In an exemplary composition, the hydrophobic/lipophilic membrane comprises about 40% phosphatidylcholine, about 3.5% phosphatidylethanolamine, about 6% phosphonophospholipids, and about 0.5% of other phospholipids. According to another embodiment, According to another embodiment the hydrophobic/lipophilic membrane of liposomes in the inventive composition comprises about 26% phosphatidylcholine, about 10% phosphatidylethanolamine, about 13% phosphonophospholipids, and about 1% of other phospholipids.

C. General Protocol for Encapsulation of Micelles or Liposomes

To a liposomal or micellular suspension, a polymer or encapsulating matrix is added to a desired concentration. If so desired a cross linking agent can be added. The polymer liposomal mixture is then dehydrated through various means, such as filtration, evaporation, freeze drying, or spray drying. The dehydrated encapsulant or film can be further milled to a desired average particle size.

The present invention uses micelles and liposomes as vehicles for delivery a cannabinoid, its analog, or both to a subject in need of treatment. The micelles and liposomes containing a cannabinoid, its analog, or both are dispersed in a pharmaceutically acceptable solvent that is suitable for a specific route of delivery to a subject in need of treatment. The inventive micellar or liposomal formulations can readily be manufactured by methods further described herein.

I. Micelle Formulation

Example 1

1 g/L Micelle Suspension of a Cannabinoid without Stabilizer

Cannabinoids were obtained from plant tissue by supercritical fluid extraction (SFE). Supercritical carbon dioxide was used as the extractant. Briefly, the plant material was contacted with carbon dioxide maintained above the critical temperature and pressure, for example, a temperature above 350 Kelvin (K) and a pressure above 150 bar to extract cannabinoids from the tissue. This cannabinoid extract was used to manufacture the inventive micellar compositions. The compositions manufactured using the protocol further described below has no added stabilizers and can be stored as a stable aqueous suspension for 3 days at 25° C.

TABLE 1

| Micelle Formulation | Ethanol Injection |
|---|---|
| Phospholipid Content | None |
| Drug Amount | 850 mg Extract |
| Drug Source | 70% THC content *Cannabis* Flower Extract obtained from supercritical CO2 extraction. |
| Injection Drug Concentration | 20 ml of 30 mg/ml THC in 95% Ethanol at 10° C. |
| Injection Type | 50 ml Syrnige w/ 22 gauge needle 50 psi 10 ml/min |
| Aqueous Medium | 195 ml Distilled H20 at 25° C. |
| Final Ethanol to Aqueous Ratio | 1:10, ethanol removed via rotor evaporation at 30 mmHg at less than 30 C. |
| Encapsulation Efficiency | >95% |
| Maximum final drug concentration in suspension | 200 mls og 1 g/l THC |
| External Stabilizer | None |
| Micell Characterisation | .2-1µ, no core apparent under oil oil immersion, stable at RT for 3 days |

Thus, 850 mg of a 70% THC *cannabis* flower extract was dissolved in 95% ethanol (20 mL) and this solution was cooled to 10° C. prior to its injection under pressure (50 psi, 10 mL/min), into 195 mL, of distilled water at 25° C. A 50 mL lurlock syringe equipped with a 22 gauge needle was used to inject the cannabinoid solution into water. The resultant aqueous micelle suspension was subjected to rotary evaporation at a reduced pressure of 30 mm mercury to remove ethanol. The temperature of the round bottom flask containing the aqueous micelle suspension was maintained below 30° C. The micelle formation efficiency using this protocol is greater than 95%. The final maximum concentration of THC in the micelles is 1 g/L of the micelle suspension. Micelles obtained using this protocol were 0.2-1.0 µm in diameter and the aqueous micelle suspension was stable for 3 days at 25° C. No aqueous core was visible under oil immersion microscopy.

Example 2

1 g/L Micelle Suspension of THC with Stabilizer

TABLE 2

| Micelle Formulation | Ethanol Injection |
| --- | --- |
| Phospholipid Content | None |
| Drug Amount | 850 mg Extract |
| Drug Source | 70% THC content *Cannabis* Flower Extract obtained from supercritical CO2 extraction. |
| Injection Drug Concentration | 20 ml of 30 mg/ml THC in 95% Ethanol at 25° C. |
| Injection Type | 50 ml Syrnige w/ 22 gauge needle 50 psi 10 ml/min |
| Aqueous Medium | 195 ml Distilled H20 at 25° C. |
| Final Ethanol to Aqueous Ratio | 1:10, ethanol removed via rotor evaporation at 30 mmHg at less than 30 C. |
| Encapsulation Efficiency | >95% |
| Maximum final drug concentration in suspension | 200 mls og 1 g/l THC |
| External Stabilizer | 0.1% w/v Guar Gum added in 10 mg portions |
| Micell Characterisation | .2-1µ, no core apparent under oil oil immersion, stable at RT for 7 days |

The cannabinoids were obtained from plant tissue using supercritical carbon dioxide as the extractant. 850 mg of a 70% THC *cannabis* flower extract was dissolved in 95% ethanol and brought to a final volume of 20 mL using 95% EtOH. The resultant solution was cooled to 10° C. and injected (50 psi, 10 mL/min), into 195 mL of distilled water (25° C.) using a 50 mL lurlock syringe equipped with a 22 gauge needle. Ethanol was removed from the resultant aqueous suspension of the micelle by rotary evaporation under a reduced pressure of 30 mm Hg to keep the temperature of this solution below 30° C. After removal of the ethanol, 0.2 g, (0.1% w/v), guar gum was added in 10 mg portions. The micelle formation efficiency is >95%, with a final maximum THC concentration of 1 g/L. The micelles obtained using this protocol were 0.2-1.0 µm in diameter and the aqueous micelle suspension was stable for 7 days at 25° C. No aqueous core was visible under oil immersion microscopy.

Micelles prepared according to this embodiment of the technology were unilamellar, as confirmed by freeze fracture electron microscopy (data not shown). As shown in FIG. 1, staining with a cannabinoid specific dye (Fast Blue) demonstrated that the membrane, and not the core of the micelles, stained with the dye. Moreover, the addition of the dye to the suspension caused immediate precipitation of the micelles. These data clearly demonstrated that the cannabinoid was entrapped in the membrane and not in the core of the micelles.

Example 3

2 g/L Micelle Suspension Using Synthesized Delta-9 THC (Dronabinol)

TABLE 3

| Micelle Formulation | Ethanol Injection |
| --- | --- |
| Phospholipid Content | None |
| Drug Amount | 420 mg D9 THC |

TABLE 3-continued

| Micelle Formulation | Ethanol Injection |
| --- | --- |
| Drug Source | Drobabinol from sigma (D9 THC) |
| Injection Drug Concentration | 20 ml of 21.0 mg/ml THC in 95% Ethanol at 10° C. |
| Injection Type | 0.17 mm stainless steel orifice at 10 ml/min at 300 psi |
| Ethanol to Aqueous Ratio | 195 ml Distilled H20 at 37° C. |
| Ethanol to Aqueous | 1:10, ethanol removed via rotor evaporation at 30 mmHg at less than 30 C. |
| Encapsulation Efficiency | >95% |
| Maximum final drug concentration in suspension | 200 mls of 2 g/l THC |
| External Stabilizer | 0.1% Guar Gum in 10 mg portions |
| Characterizaton | .1-.5µ, no core apparent un oil immersion, stable a RT for 1 week |

10.5 g Dronabinol was dissolved 95% ethanol (final volume 20 mL). The solution was cooled to 10° C. and injected through a 0.17 mm stainless steel orifice at 300 psi into 195 mL, of distilled water at 37° C. The resultant aqueous suspension micelles was subjected to rotary evaporation at 30 mm Hg to remove ethanol at a solution temperature below 30° C. After removal of the ethanol, 0.2 g, (0.1% w/v), guar gum was added in 10 mg portions. The micelle formation efficiency using this protocol was greater than 95% and the final concentration of THC was 2 g/L. Micelles 0.1-0.5 µm in diameter were obtained and this aqueous micelle suspension was stable for 7 days at 25° C. No aqueous core was visible under oil immersion microscopy.

Example 4

2 g/L Micelle Suspension using a Mixture of Cannabinoids

TABLE 4

| Micelle Formulation | Ethanol Injection |
| --- | --- |
| Phospholipid Content | None |
| Drug Amount | 200 mg THC, 110 mg CBD, 110 mg CBC |
| Drug Source | Synthsised In House |
| Injection Drug Concentration | 20 ml of 21.0 mg/ml Cannabinpoids in 95% Ethanol at 25° C. |
| Injection Type | Ultrasonic Atomizer Nozzle @ 60 Hz, 20 um drop size, 10 ml/min |
| Aqueous Medium | 195 ml PBS at 25° C. |
| Ethanol to Aqueous Ratio | 1:10, ethanol removed via rotor evaporation at 30 mmHg at less than 30 C. |
| Encapsulation Efficiency | >95% |
| Maximum final drug concentration in suspension | 200 mls of 1 g/L THC, 0.5 g/l CBD, 0.5 g/l CBC |
| External Stabilizer | 0.1% Guar Gum in 10 mg portions |
| Characterizaton | 50-200 nm, no core apparent un oil immersion, stable a RT for 4 weeks |

200 mg of chemically synthesized THC was combined with 110 mg chemically synthesized CB and 110 mg synthetic CBC and the mixture was dissolved in 95% ethanol (final volume of 20 ml) The resultant solution was cooled to 10° C. and injected using an Ultrasonic Atomizer Nozzle at 60 Hz (20 µm drop size, 10 mL/min), into 195 mL, of distilled water (37° C.). Ethanol was removed from the resultant aqueous suspension of the micelle by rotary evaporation under a reduced pressure of 30 mm Hg to keep the temperature of this solution below 30° C. The final volume of this solution was 200 mL. To this solution was added 0.2 g, (0.1% w/v), guar gum in 10 mg portions. The micelle formation efficiency using this method was >95%. The final maximum cannabinoid concentration was 2 g/L and micelles 50-200 nm in diameter were obtained. The aqueous micelle suspension was stable for 4 weeks at 25° C.

II. Liposome Formulation

Example 5

50 g/L Liposomal Suspension of THC

TABLE 5

| Micelle Formulation | Ethanol Injection |
|---|---|
| Lipid Amount | 15 grams Ethanolic Soluable Soy Lecithin 50 |
| Lipid Content | Phosphatidylcholine (PC) ~52%, Phosphatidylethanolamine (PE) ~20%, Phospholipids (PPL) ~26%, other ~2% |
| Drug Amount | 15 grams |
| Drug Source | 70% THC content Cannabis Flower Extract obtained from supercritical CO2 extraction. |
| Ethanol Injection | 60 ml of 250 mg/ml THC, 130 mg/ml PC, 50 mg/ml PE, 65 mg/ml PPL in 95% Ethanol at 10° C. |
| Injection Type | 100 ml Syrnige w/ 22 gauge needle 50 psi 10 ml/min |
| Aqueous Medium | 540 ml Distilled H20 at 25° C. |
| Final Ethanol to Aqueous Ratio | 1:10, ethanol and water removed via rotor evaporation at 30 mmHg at less than 55 C. take to a final volume of 200 ml |
| Encapsulation Efficiency | >95% |
| Maximum final drug concentration in suspension | 200 mls of 50 g/l THC |
| External Stabilizer | None |
| Micell Characterisation | diameter 200-400 nm, aqueous core apparent under oil immersion, stable at RT for >3 months |

15 g of a 70% THC *cannabis* flower extract obtained using supercritical $CO_2$ extraction was dissolved in 95% ethanol (final volume of 30 ml). This ethanolic extraction solution was combined with an ethanolic solution of Lecithin-50 (30 ml), which was prepared by dissolving 15 grams of Lecithin-50 using small portions of 95% EtOH and bringing the final volume of the lipid/EtOH solution to 30 mL using 95% EtOH. The ethanolic solution of lipid and THC was cooled to 10° C. and injected at a pressure of 50 psi (10 mL/min), into 540 mL of distilled water (25° C.), using a 100 mL lurlock syringe equipped with a 22 gauge needle. A pressure of 50 psi, and a flow rate of 10 mL/min was maintained during the injection process. The liposomal suspension was concentrated to 200 mL by rotary evaporation at 30 mm Hg keeping the temperature of the liposomal suspension below 55° C. The liposome formation efficiency using this protocol was greater than 95%. The final maximum THC concentration was 50 g/L. Liposomes 200-400 nm in diameter were obtained and had an aqueous core visible under oil immersion microscopy. The aqueous liposomal suspension was stable for more than 3 months at 25° C.

Figure 2:
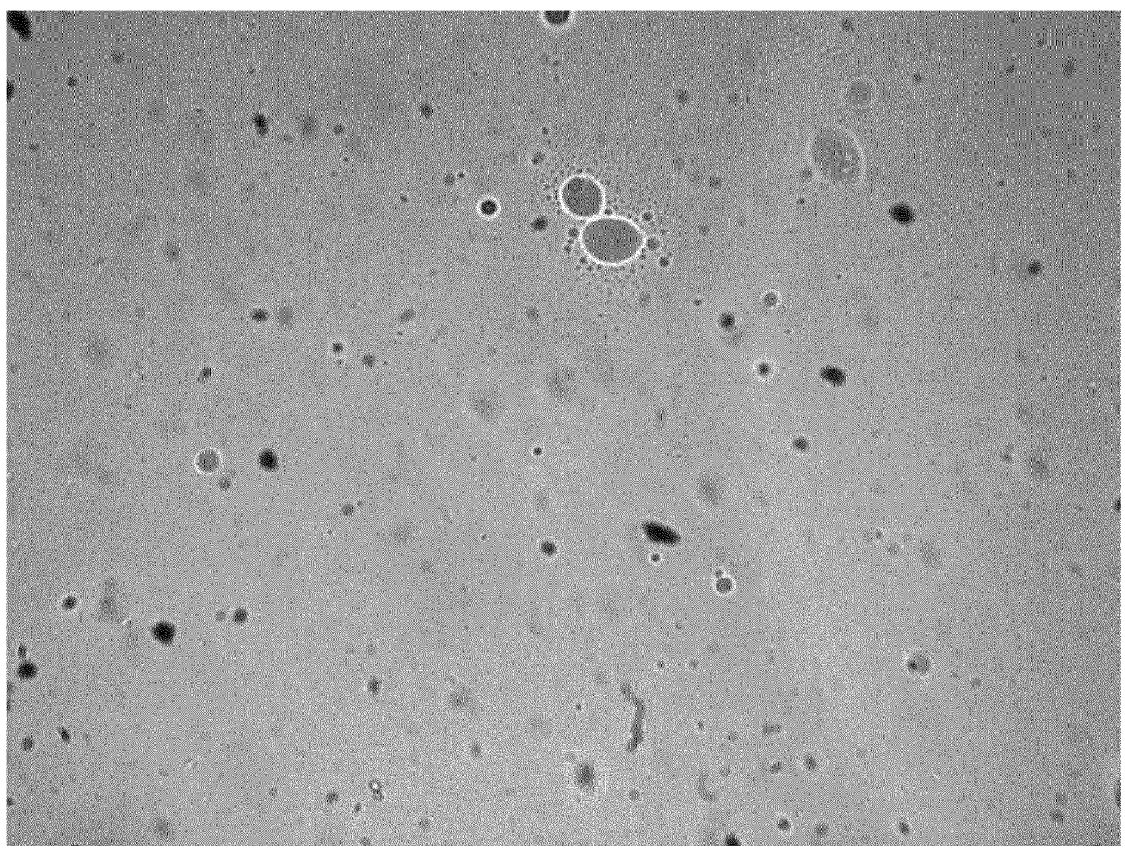
FIG. 2 provides an oil immersion image of an unstained liposomal suspension.
Figure 3:
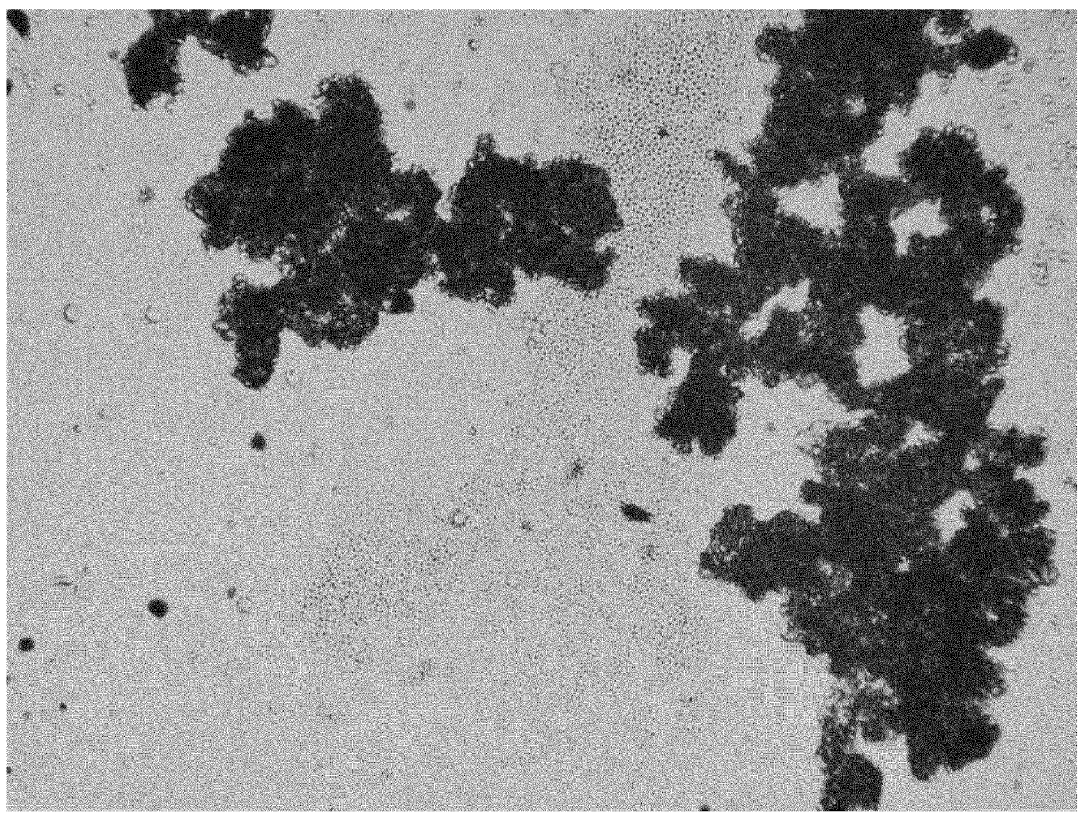
FIG. 3 provides an oil immersion image of a liposomal suspension stained with fast blue as seen through a red filter. The stain condensates on the outer liposome membrane.

The liposomes have a size of about 0.22 um, as determined by gel filtration, and a spherical shape, as demonstrated by oil immersion light microscopy (FIG. 2), and are unilamellar, as shown by freeze fracture electron microscopy (data not shown). As shown in FIG. 3, staining with a cannabinoid specific dye (Fast Blue) demonstrated that the membrane, and not the core of the liposomes, stained with the dye. These data clearly demonstrated that the cannabinoid was entrapped in the membrane and not in the core of the liposomes.

Example 6

50 g/L Liposomal Suspension of Pure Delta-9-THC

TABLE 6

| Micelle Formulation | Ethanol Injection |
|---|---|
| Lipid Amount | 10.5 grams Ethanolic Soluable Soy Lecitein 80 |
| Lipid Content | Phosphatidylcholine (PC) ~81%, Phosphatidylethanolamine (PH) ~7.5%, Phospholipids (PPL) ~11%, other ~0.5% |
| Drug Amount | 10.5 grams |
| Drug Source | Drobabinol from sigma (D9 THC) |
| Ethanol Injection | 40 ml of 262.5 mg/ml THC, 212 mg/ml PC, 19.6 mg/ml PF, 28.8 mg/ml PPL in 95% Ethanol at 30° C. |
| Injection Type | 0.17 mm stainless steel orifice at 10 ml/min at 300 psi |
| Aqueous Medium | 360 ml Distilled H20 at 25° C. |
| Final Ethanol to Aqueous Ratio | 1:10, ethanol and water removed via rotor evaporation at 30 mmHg at less than 55 C., take to a final volume of 200 ml |
| Encapsulation Efficiency | >95% |
| Maximum final drug concentration in suspension | 200 mls of 50 g/l THC |
| External Stabilizer | None |
| Micell Characterisation | diameter 20-250 nm, aqueous core apparent under oil immersion, stable at RT for >3 months |

10.5 g of Dronobinol was dissolved in a portion of 95% ethanol (EtOH) and the final volume of this solution was brought to 20 ml using 95% EtOH. This ethanolic solution was combined with 20 ml of an ethanolic solution of soluble soy lecithin-80 which was prepared by dissolving 10.5 grams of Lecithin-80 into a portion of 95% EtOH and adjusting the volume of the lipid/EtOH solution to 20 mL using 95% EtOH. The resultant solution was cooled to 30° C. and injected through a 0.17 mm stainless steel orifice at 300 psi into 360 mL of distilled water (25° C.). Concentration of the ethanolic/aqueous liposomal suspension to 200 mL by rotary evaporation at 30 mm Hg to keep the temperature below 55° C. gave the desired liposomal composition. The liposome formation efficiency was >95% and the final concentration of THC was 50 g/L.

Liposomes 20-250 nm in diameter were obtained and had an aqueous core visible under oil immersion microscopy. The aqueous liposomal suspension was stable for more than 3 months at 25° C.

Example 7

40 g/L Liposomal Suspension of a Mixture of Cannabinoids

TABLE 7

| Micelle Formulation | Ethanol Injection |
|---|---|
| Lipid Amount | 126 grams Ethanolic Soluable Soy Lecitein 80 |
| Lipid Content | Phosphatidylcholine (PC) ~81%, Phosphatidylethanolamine (PH) ~7.5%, Phospholipids (PPL) ~11%, other ~0.5% |
| Drug Amount | 15.75 g THC, 7.875 g CBD, 7.875 g CBC |
| Drug Source | Synthsised In House |

TABLE 7-continued

| Micelle Formulation | Ethanol Injection |
|---|---|
| Ethanol Injection | 200 ml of 77.5 mg/ml THC, 39.375 mg/ml CBD, 39.375 mg/ml CBC, 510 mg/ml PC, 47.25 mg/ml PF, 69.3 mg/ml PPL in 95% Ethanol at 25° C. |
| Injection Type | Ultrasonic Atomizer Nozzle @ 60 Hz, 20 um drop size, 10 ml/min |
| Aqueous Medium | 1.2 L Distilled H20 at 25° C. |
| Final Ethanol to Aqueous Ratio | 1:7, ethanol and water removed via rotor evaporation at 30 mmHg at less than 55 C., take to a final volume of 500 ml |
| Encapsulation Efficiency | >95% |
| Maximum final drug concentration in suspension | 750 mls of 21 g/l THC, 10 g/L CBD, 10 g/L CBC |
| External Stabilizer | None |
| Micell Characterisation | diameter 20-100 nm, aqueous core apparent under oil immersion, stable at RT for 24 H |

15.75 g of a 2:1:1 (w:w:w) ratio of THC, CBD, CBC were dissolved in a portion of 95% ethanol and brought to a final volume of 100 mL with 95% EtOH. This ethanolic solution was combined with an ethanolic solution of soluble soy Lecithin-80 (100 mL) which was prepared by dissolving 126 g of Lecithin-80 into a portion of 95% EtOH and bringing the volume of the lipid/EtOH solution to 100 mL. The resultant mixture was cooled to 25° C. and injected using an Ultrasonic Atomizer Nozzle at 60 Hz (20 μm drop size, 10 mL/min), into 1.20 L of distilled water (25° C.). The ethanolic-aqueous liposomal suspension was concentrated by rotary evaporation at 30 mm Hg and a temperature below 55° C. to a final volume of 200 mL. The liposome formation efficiency was >95% and the final maximum concentration of THC was 40 g/L. Liposomes 20-100 nm in diameter and having an aqueous core visible under oil immersion microscopy were obtained. The aqueous liposomal suspension was stable for more than 3 months at 25° C.

III. Encapsulation Formulations

Example 8

Calcium Alginate Encapsulated Liposomal Suspensions of Cannabinoids

TABLE 8

| Example 8: Encapulation of Liposomal suspension of Plant Extract | Componets |
|---|---|
| Liposmal Suspension Source | Example 5 |
| Liposome Drug Concentration | 50 g/L |
| Encapulant | Sodium Alginate |
| Encapsulant Concentration | 2% or 20 g/L |
| Addition Method | Bulk Addition |
| Crosslinking Agent | CaCl2 |
| Cross Linking agent concentration | 40 mls of 25% |
| Crosslinking Incubation | 10 mins |
| Drying conditions | Warm Air 50 C. for 24 H |
| Final Product Description | ~25 g Free Flowing Powder, disloves in buffered H20 |
| Content | 10 g d9 THC, 10 g Lethicin 50, 4 g Alginate |
| Active Drug Content | ~40% |
| Release Profile | 100% in 60 mM citrate pH 7.0 |

4 g of sodium alginate was dissolved in 200 mL of a 50 g/L liposomal suspension (Example 5) of THC. The alginate/THC mixture was poured into 40 mL of a stirring 25% aqueous solution of calcium chloride. The resultant solution was further stirred for an additional 10 mins to allow crosslinking (polymerization) of alginic acid. The solid mass of calcium alginate encapsulated THC liposomal suspension is cold pressed to remove the majority of the water. The pressed material is further dried in warm air, 50° C., for 24 hrs. This air-dried material is milled to a free flowing yellowish white powder that readily dissolves in buffered water. The cannabinoid content of the alginate powder is ~40%, and the entrapped material is completely released in 60 mM, pH 7, citrate buffer.

Example 9

Film Formation of Liposomal Suspension

TABLE 9

| Example 9: Film Formation of Liposomal suspension from pure D9 THC | |
|---|---|
| Liposmal Suspension Source | Example 6 |
| Drug Concentration | 50 g/L |
| Encapulant | Sodium Alginate or Agarose or Gelatin or pectin |
| Encapsulant Concentration | 4% or 40 g/L |
| Crosslinking Agent | none |
| Cross Linking agent concentration | None |
| Crosslinking Incubation | None |
| Drying conditions | Freeze Drying or Spray Drying |
| Final Product Description | Free Flowing Powder disloves in H20 |
| Content | 10 g d9 THC, 10 g Lethicin 50, 8 g Alginate (or other encapsulant) |
| Active Drug Content | ~20% |
| Release Profile | 100% in distilled H20 |

To the liposomal suspension prepared using the protocol of Example 6 was added sodium alginate in a amount sufficient to provide a 4% w/v (8 grams) solution of alginate in liposomal suspension. The suspension is stirred at room temperature to dissolve the alginate. Once dissolved the entire suspension is shell frozen over a dry ice/acetone bath and freeze dried to a solid mass which is milled to a free flowing powder. Yield 28 grams. The powder thus obtained contains ~40% cannabinoids and dissolves completely in distilled water.

Example 10

Calcium Alginate Encapsulated Liposomal Suspension of Mixed Cannabinoids

TABLE 10

| Example 10: Encapsulation of Liposomal suspension of Mixed Cannabinoid Formulation | |
|---|---|
| Liposmal Suspension Source | Example 7 |
| Drug Concentration | 21 g/L THC 10 g/L CBD, 10 g/L CBC |
| Encapulant | Sodium Alginate |
| Encapsulant Concentration | 4% or 20 g/L |
| Addition Method | Injection through .17 um orfice 1 ml/min |
| Crosslinking Agent | CaCl2 |
| Cross Linking agent concentration | 40 mls of 25% |
| Crosslinking Incubation | 10 mins |
| Drying conditions | Warm Air 50 C. for 24 H |
| Final Product Description | Free Flowing Power, disloves in H20 |

TABLE 10-continued

Example 10: Encapsulation of Liposomal suspension of Mixed Cannabinoid Formulation

| | |
|---|---|
| Content | 15.0 g d9 THC, 7.5 g CBD, 7.5 g CBC, 120 g Lethicin 80, 15 g Alginate |
| Active Drug Content | ~9.5% THC, ~4.7% CBD, ~4.7% CBC |
| Release Profile | 100% in 60 mM citrate ph 7.0 |

To the liposomal suspension of mixed cannabinoids containing 15.0 g THC, 7.5 g CBD, 7.5 g CBC and 120 g Lecithin-80 (Example 7), was added 4 g of sodium alginate. The resultant solution was injected through a 0.17 mm stainless steel orifice at 300 psi into 40 mL of a stirring solution of 25% aqueous calcium chloride. The resultant solution was further stirred for an additional 10 mins to allow crosslinking (polymerization) of alginic acid. The solid mass of calcium alginate encapsulated THC liposomal suspension is cold pressed to remove the majority of the water. The pressed material is further dried in warm air, 50° C., for 24 hrs. This air-dried material is milled to a free flowing yellowish white powder that readily dissolves in buffered water.

The cannabinoid content of the alginate powder is ~9.5% THC, ~4.7% CBD, ~4.7% CBC, and these compounds were completely released in 60 mM, pH 7, citrate buffer.

Example 11

Formation of a Dispersible Delta-9-THC Dry Powder

TABLE 11

Example 11: Dispersiable Dry Power D9 THC Liposmal Preparation

| | |
|---|---|
| Liposmal Suspension Source | Example 6 |
| Drug Concentration | Diluted 1:10 to 200 ml of 5 g/L |
| Encapulant | Lactose or Sucrose |
| Encapsulant Concentration | 200 mg/ml Lactose or Sucrose, 0.6 mg/ml L-Lucine or Isolucine |
| Crosslinking Agent | none |
| Cross Linking agent concentration | None |
| Crosslinking Incubation | None |
| Drying conditions | Spray Drying or Freeze Drying |
| Final Product Description | 42.5 grams white Free Flowing Powder, disloves in H2O |
| Content | 1 g d9 THC, 1 g Lethicin 50, 40 grams Lactose, 0.12 L Lucine |
| Active Drug Content | ~2.3% |
| Release Profile | 100% in distilled H2O |

The liposomal preparation from Example 6 was diluted 1:10 with distilled water. To 200 ml of the resulting solution was added lactose or sucrose in an amount sufficient to provide a 200 mg/ml (40 grams) solution of these reagents. L-lucine in an amount of 0.6 mg/ml (0.12 grams) was then added to the reaction mixture. The resultant solution was frozen using a dry ice/acetone bath and freeze dried to obtain a solid mass. Alternatively the solution can be spray dried with a forced air spray dryer at a temperature of 55° C. The crystalline solid thus obtain was milled to a free flowing powder. Approximately 42 grams of resulting powder containing approximately 1 g of THC, (i.e., a solid composition having a cannabinoid content of ~2.3%) was obtained. This powder dissolves completely in water releasing the liposomes. The resulting suspension contains >90% of the starting liposomes.

What is claimed is:

1. A method of producing a suspension of particles of one or more cannabinoids in aqueous media consisting of the steps of:
    (a) dissolving one or more cannabinoids in ethanol to obtain an ethanol cannabinoid solution;
    (b) injecting the ethanol cannabinoid solution into distilled water; and
    (c) removing the ethanol from the composition from step (b), thereby producing a suspension of particles of one or more cannabinoids in aqueous media;
    (d) optionally adding stabilizer after the ethanol has been removed;
    wherein the particles of one or more cannabinoids show no aqueous core under oil immersion microscopy.

2. The method of claim 1, wherein the average particle diameter in the aqueous cannabinoid suspension is in a range between 50 and 1000 nm, and wherein the concentration of cannabinoids in the aqueous cannabinoid suspension is from about 1.0 g/liter to about 2 g/liter.

3. The method of claim 1, wherein the one or more cannabinoids are selected from the group consisting of natural compounds, synthetic compounds, semi-synthetic compounds, and mixtures thereof.

4. The method of claim 3, wherein the one or more cannabinoids are selected from the group consisting of cannabinol, cannabidiol, Δ9-tetrahydrocannabinol, Δ8-tetrahydrocannabinol, 11-hydroxy-tetrahydrocannabinol, 11-hydroxy-Δ9-tetrahydrocannabinol, levonatradol, Δ11-tetrahydrocannabinol, tetrahydrocannabivarin, dronabinol, amandamide, nabilone, and combinations thereof.

5. The method of claim 1 wherein the stabilizer is present and is guar gum.

6. A method of producing a suspension of particles of one or more cannabinoids in aqueous media consisting of the steps of:
    (a) providing plant material from a *cannabis* plant;
    (b) subjecting the plant material from step (a) to supercritical fluid extraction to obtain an extract of cannabinoids;
    (c) dissolving the extract of step (b) in ethanol to obtain an ethanol cannabinoid solution;
    (d) injecting the ethanol cannabinoid solution into distilled water; and
    (e) removing the ethanol from the composition from step (d), thereby producing a suspension of particles of one or more cannabinoids in aqueous media;
    (f) optionally adding stabilizer after the ethanol has been removed;
    wherein the particles of one or more cannabinoids show no aqueous core under oil immersion microscopy.

7. The method of claim 6, wherein the average particle diameter in the aqueous cannabinoid suspension is in a range between 50 and 1000 nm, and wherein the concentration of cannabinoids in the aqueous cannabinoid suspension is from about 1.0 g/liter to about 2 g/liter.

8. The method of claim 6 wherein the stabilizer is present and is guar gum.

* * * * *